United States Patent [19]

Ferris et al.

[11] Patent Number: 5,220,921
[45] Date of Patent: Jun. 22, 1993

[54] NONMAGNETIC TACTILE STIMULATOR AND BIOMAGNETOMETER UTILIZING THE STIMULATOR

[75] Inventors: Johathan R. Ferris, Escondido; K. Randy Brimhall, San Diego; Frank W. Vanesky, Vista; D. Scott Buchanan, Escondido; Laurence Warden, San Diego, all, Calif.

[73] Assignee: Biomagnetic Technologies, Inc., San Diego, Calif.

[21] Appl. No.: 783,109

[22] Filed: Oct. 25, 1991

[51] Int. Cl.⁵ ............................................. A61B 5/05
[52] U.S. Cl. .............................. 128/653.1; 128/731; 128/744; 324/248; 324/262
[58] Field of Search ............... 128/653.1, 653.2, 653.5, 128/774, 782, 731, 741, 742, 744, 905; 324/244, 248, 260, 262; 600/27

[56] References Cited

U.S. PATENT DOCUMENTS

| | | | |
|---|---|---|---|
| 4,387,723 | 6/1983 | Atlee, III et al. | 128/741 |
| 4,503,863 | 3/1985 | Katims | 128/741 |
| 4,793,355 | 12/1988 | Crum et al. | 128/713 |
| 5,018,724 | 5/1991 | Naser et al. | 128/653.1 |
| 5,022,407 | 6/1991 | Horch et al. | 128/742 |
| 5,027,819 | 7/1991 | Crum | 128/653.1 |
| 5,081,071 | 1/1992 | Hirschkoff | 128/653.1 |
| 5,152,288 | 10/1992 | Hoenig et al. | 128/653.1 |

*Primary Examiner*—Lee S. Cohen
*Assistant Examiner*—Krista Pfaffle
*Attorney, Agent, or Firm*—Gregory Garmong

[57] ABSTRACT

An apparatus for making bioelectromagnetic measurements of the human body includes an apparatus for measuring the bioelectromagnetic reaction of a living body to a tactile stimulation and a tactile stimulator that controllably applies a tactile stimulation to the body without creating a magnetic or electrical field that is detected directly by the apparatus for measuring the bioelectromagnetic reaction. The tactile stimulator includes a pressure chamber closed on one side by a movable body such as a piston or flexible membrane, a conduit that transmits pneumatic pressure to the pressure chamber, and apparatus for applying pneumatic pressure to the conduit. The measuring apparatus, such as a biomagnetometer, may be located within a shielded room, and in this case the pressure chamber and movable body are preferably located within the shielded room, the apparatus for applying pneumatic pressure is located outside the room, and the conduit passes from the exterior to the interior of the room.

19 Claims, 4 Drawing Sheets

NONMAGNETIC TACTILE STIMULATOR AND BIOMAGNETOMETER UTILIZING THE STIMULATOR

BACKGROUND OF THE INVENTION

This invention relates to the measurement of small magnetic fields produced by the body, and, more particularly, to stimulating tactile sensations in the body so that the resulting magnetic fields produced by the body may be measured.

The biomagnetometer is a device that measures the very small magnetic fields produced by the body. The magnetic fields, particularly those produced by electrical currents flowing in the brain and the heart, can be important indicators of the health of the body, because aberrations in the magnetic field can be associated with certain types of disfunctions either for diagnosis or early prediction. Moreover, the magnetic fields produced by the brain are an indicator of thought processes and the location at which such processes occur, and can be used to investigate the mechanisms of thought.

Magnetic fields produced by the body are very small, because they result from very small electrical current flows. Typically, the strength of the magnetic field produced by the brain is about 0.00000001 Gauss. by comparison, the strength of the earth's magnetic field is about 0.5 Gauss, or over ten million times larger than the magnetic field of the brain.

The biomagnetometer must therefore include a very sensitive detector of magnetic fields. Current biomagnetometers utilize a pickup coil which produces an electrical current when a magnetic field penetrates the pickup coil. The electrical current, which is typically very small in magnitude, is detected by a Superconducting QUantum Interference Device, also known by the acronym SQUID. Spurious effects from the detection of other magnetic fields than those produced by the brain can be removed by appropriate filters. However, the ability of filters to remove all of the extraneous effects is limited. To further improve the signal-to-noise ratio of the system, the subject and pickup coil can be located in a magnetically shielded room. The operation of SQUIDS and their electronics are disclosed in U.S. Pat. Nos. 3,980,076; 4,079,730; 4,386,361; and 4,403,189. A biomagnetometer is disclosed in U.S. Pat. No. 4,793,355. A magnetically shielded room is disclosed in U.S. Pat. No. 3,557,777. The disclosures of all of these patents are incorporated herein by reference.

The biomagnetometer is often used to measure the magnetic fields produced by the brain either spontaneously (without an external stimulus) or in response to an external stimulus. In the latter case, the external stimulus can be a visual stimulus, an auditory stimulus, a tactile (touch) stimulus, or other stimulus of interest. The present invention is concerned with the production of tactile stimuli and the measurement of the response of the body to such stimuli.

It is common practice to induce tactile stimulation by attaching a small electrode to the body of the subject, and controllably applying a small voltage to the electrode. The body of the subject reacts to the small electrical shock, and that response is measured by the biomagnetometer. Although this approach is operable in one respect, it produces a particular shock response rather than a mechanical touch response which may be of interest. Also, the established technique requires that an electrical signal be conducted into the magnetically shielded room. While the current is small, it is sufficient that the resulting magnetic field can be detected by the biomagnetometer. The detection of this stimulating signal interferes with the measurement of the biomagnetic signal resulting from the stimulation. A shock, even if relatively small, can be uncomfortable for the subject, particularly if the shock is applied in a sensitive region such as the face. Apprehension of the shock may itself produce measurable biomagnetic signals.

There is a need for an improved approach for controllably inducing tactile stimulation in the body of a person, in such a manner that there is no magnetic field produced that interferes with the biomagnetic measurement of the response to the stimulus. The present invention fulfills this need, and further provides related advantages.

SUMMARY OF THE INVENTION

The present invention provides a tactile stimulator and measurement apparatus utilizing the tactile stimulator in measuring bioelectromagnetic responses of a person to the tactile stimulation. The tactile stimulator provides a controllable, positive mechanical force and stimulation to the surface of the skin of a person, without inducing any bioelectromagnetic field that can be detected directly by the measurement apparatus. The apparatus therefore detects only the response produced in the person by the stimulation, not the mixture of response and magnetic field produced by the act of stimulation. The tactile stimulator is not painful or uncomfortable to most persons, removing another distracting influence.

In accordance with the invention, apparatus for measuring reactions of a living body comprises means for measuring the bioelectromagnetic reaction of a living body to a tactile stimulation, and means for controllably stimulating a tactile sensation on the surface of the body without creating a signal that may be detected directly by the means for measuring. The apparatus may make biomagnetic measurements of the body, and in this case the means for measuring comprises biomagnetometer means including a magnetic field sensing coil for measuring magnetic fields arising from the body. Instead or in addition, the apparatus may make electrical measurements of the body, and in this case the means for measuring comprises a detector of electrical signals.

The means for controllably stimulating is preferably a tactile stimulator that is attachable to the body, which controllably applies a mechanical force against the body without creating a field that is directly detectable by the measuring means. A preferred form of tactile stimulator includes a pressure chamber closed on one side by a movable body such as a piston or flexible membrane, a conduit that transmits pneumatic pressure to the pressure chamber, and a pneumatic pressure source that pressurizes the interior of the conduit.

The subject person and at least a pickup portion of the measurement means may be located within a shielded room, such as a magnetically shielded room (MSR). In this embodiment, the pressure chamber and movable body of the tactile stimulator are located inside the shielded room, the pressure source is located outside the shielded room, and the conduit extends through the wall of the shielded room to conduct the pressure from the exterior to the interior. Since the pressure source usually includes an electric solenoid which generates magnetic and/or electric fields as it operates, locating the pressure source exterior to the shielded room prevents the measurement means from detecting the operation of the pressure source directly. The fluid pressure conduit that extends into the interior of the shielded room and the portion of the apparatus that are positioned in the shielded room have no associated magnetic and/or electrical field.

The tactile stimulator therefore is operable to produce mechanical force on the skin and body of the subject, and permit the brain response to that force to be measured without interference from the stimulation apparatus. Although the need for such a tactile stimulator for biomagnetic measurements prompted the present invention, it is also useful where the electrical response to the stimulus is measured. Other features and advantages of the invention will be apparent from the following more detailed description of the preferred embodiment, taken in conjunction with the accompanying drawings, which illustrate, by way of example, the principles of the invention.

DETAILED DESCRIPTION OF THE PREFERRED EMBODIMENT

Figure 1:
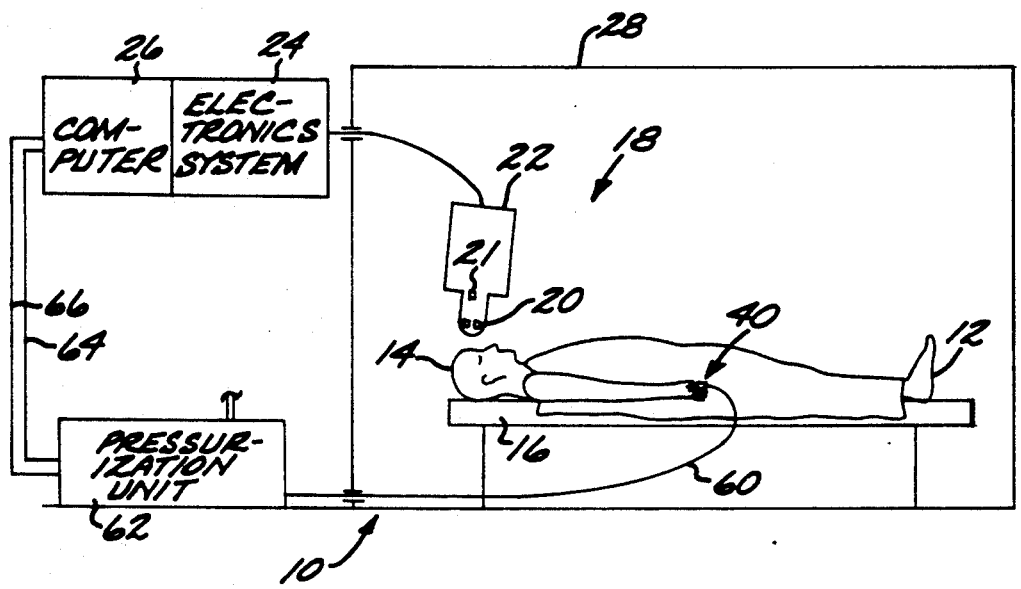
FIG. 1 is a schematic elevational view of an apparatus in accordance with the invention, with a subject in position for a biomagnetic measurement.

As illustrated in FIG. 1, the present invention is preferably embodied in an apparatus 10 for obtaining biomagnetic data from the body 12 of a human patient or subject. More specifically, the data is normally obtained from biomagnetic sources within the head 14 of the person. The person lies upon a table 16 in proximity to a biomagnetometer 18. The biomagnetometer 18 includes a plurality of magnetic field sensing coils 20 for measuring small magnetic fields. The output signal of each magnetic field sensing coil 20 is detected by a detector, preferably a superconducting quantum interference device 21 (SQUID). Both the magnetic field sensing coil 20 and the SQUID 21 are maintained at a cryogenic operating temperature within a dewar 22. In the preferred practice a large number of pairs of sensing coils 20 and SQUIDs 21 are located in the dewar 22. This apparatus 10 gives good spatial resolution of the biomagnetic signals for reconstruction of their origin in space. Multiple dewars may also be used.

The magnetic signals from the brain are picked up by the magnetic field sensing coils 20 in the dewar 22, and the signals are detected by the SQUIDs 21. The SQUIDs 21 detect the magnetic field values as electrical currents that are processed in an electronics system 24 and stored in a computer 26 as a function of time. The sensors 20 and the body 12 of the patient are preferably, but not necessarily, enclosed within an enclosure 28 (also termed a magnetically shielded room or MSR) that shields the apparatus and magnetic field source from external magnetic influences. By screening off the external influences, the amount of signal processing and filtering required to obtain a meaningful indication of the biomagnetic field is reduced.

Figure 2:
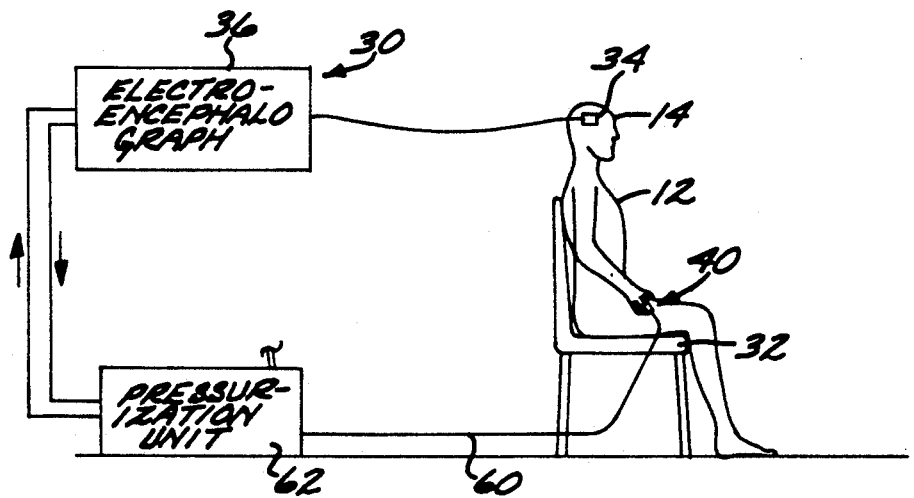
FIG. 2 is a schematic elevational view of another apparatus in accordance with the invention, with a subject in position for an electroencephalogram.

The tactile stimulator of the invention may also be used for measurements of electrical signals produced by the brain (or other portions of the subject's body). An electroencephalograph (EEG) apparatus 30 for measuring electrical signals is shown in FIG. 2. The body 12 is placed into a chair 32 with a sensor 34 fastened to the head 14. Electrical signals from the brain are measured with an electroencephalograph 36.

Biomagnetic and bioelectric measurements are collectively termed bioelectromagnetic measurements herein.

In some studies and diagnostic procedures, it is desirable to apply a mechanical or tactile stimulation to the body 12 of the person, and then record the brain response using the biomagnetometer 18 or the electroencephalograph 36. A tactile stimulator 40 that accomplishes the mechanical stimulation is illustrated in relation to the body in FIGS. 1 and 2, in more detail in FIG. 3. The tactile stimulator 40 does not itself emit magnetic or electrical fields that can be detected directly by the biomagnetometer or the electroencephalograph, because the portion of the tactile stimulator within detection range of the measurement apparatus does not produce magnetic or electrical fields at all, and the portion which does produce magnetic or electrical fields is located remotely. The term "directly" in respect to detection of fields means that the tactile stimulator 40 does not produce fields that are themselves picked up by the measurement apparatus. Instead, the tactile stimulator 40 stimulates the body of the person, who reacts. It is the magnetic field or electrical field produced by the reaction in the brain or other part of the body that is detected by the biomagnetometer or EEG.

Figure 3:
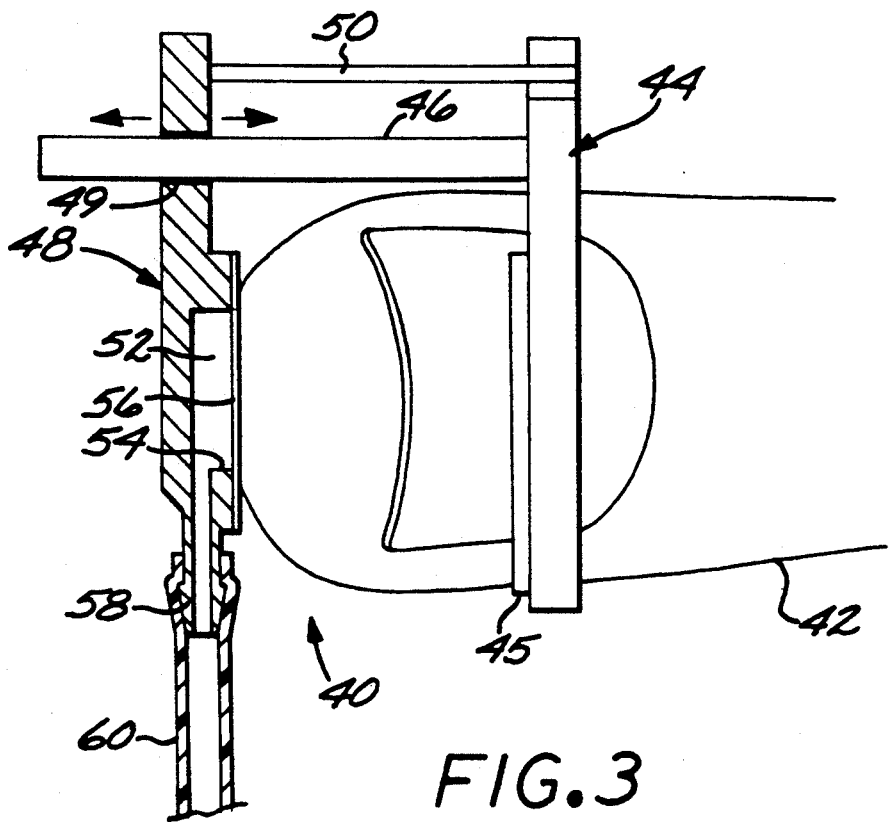
FIG. 3 is an end view of a finger with the tactile stimulator attached thereto, with one embodiment of the tactile stimulator shown in section.

The tactile stimulator 40 is illustrated in FIG. 3 attached to a finger 42 of the body 12 with a particular attachment structure, but it can be readily attached to other body parts using suitable attachments or other convenient attachment means, such as a Velcro ® strip, tape, plastic tie, or adhesive, for example. In the illustrated attachment to the finger 42, a plastic piece 44 is placed against the back side of the finger 42. A rubber pad 45 is positioned between the plastic piece 44 and the finger 42, for comfort and to achieve a solid fit. A plastic beam piece 46 extends perpendicular to the plastic piece 44, and engages a body 48 of the tactile stimulator 40 through a slip joint 49. An elastic band 50 extending between the plastic piece 44 and the body 48 holds the tactile stimulator 40 against the finger 42. When pressure is applied to the tactile stimulator 40, the slip joint 49 binds and prevents the stimulator from moving away from the finger.

The body 48 includes a hollow portion that serves as a pressure chamber 52. The pressure chamber 52 has an opening 54 positioned adjacent to the finger 42. A flexible membrane 56 attached to the body 48 covers the opening 54 of the pressure chamber 52 and seals the pressure chamber 52. The body 48 is preferably constructed of a moldable plastic such as thermoplastic polyurethane. The flexible membrane 56 is preferably constructed of flexible thermoplastic polyurethane about 0.005 inches thick. The flexible membrane 56 is ultrasonically welded to the body 48 so as to cover the opening 54. The exterior surface of the flexible membrane 56, which contacts the finger 42, may be made smooth as shown in FIG. 3, or with a probe as will be discussed in relation to the embodiment of FIG. 4.

A suitable external pressure connector such as a nipple 58 is formed in the body 48, to provide pneumatic communication to the interior of the pressure chamber 52. A conduit 60, such as a flexible plastic tube, attaches to the nipple 58. The conduit 60 transmits pneumatic pressure, either liquid or gas but preferably gas, from a remote pressurization unit 62 (FIGS. 1 and 2) to the tactile stimulator 40 and in particular to the interior of the pressure chamber 52.

A pneumatic pressure applied to the conduit 60 by the pressurization unit 62 is transmitted to the interior of the pressure chamber 52. The pressure to be applied, or a series of pressures to be applied, is provided to the pressurization unit 62 as a command signal 64 from the computer 26, and a feedback response signal 66 is sent from the pressurization unit 62 to the computer 26.

The applied pressure causes the flexible membrane 56 to flex outwardly, against the body of the person, and in the illustrated example against the finger 42 of the person. The person experiences a sensation of pressure, which is manifested in responsive bioelectromagnetic signals produced in the brain or elsewhere. These signals are sensed by the measurement apparatus 18 or 30. If the pressure is removed, the membrane 56 flexes back to its original position, removing the pressure and the tactile sensation. In this manner, the flexible membrane 56 is moved from a first position whereat it is forced against the finger 42, and a second position whereat it is relaxed away from forced contact against the finger 42. The nature of the sensation can be varied by changing the pressure, applying a series of varied pressures in a particular selected pattern that is provided to the pressurization unit 62, or by using a textured external surface on the flexible membrane or a probe having a shaped end.

Figure 4:
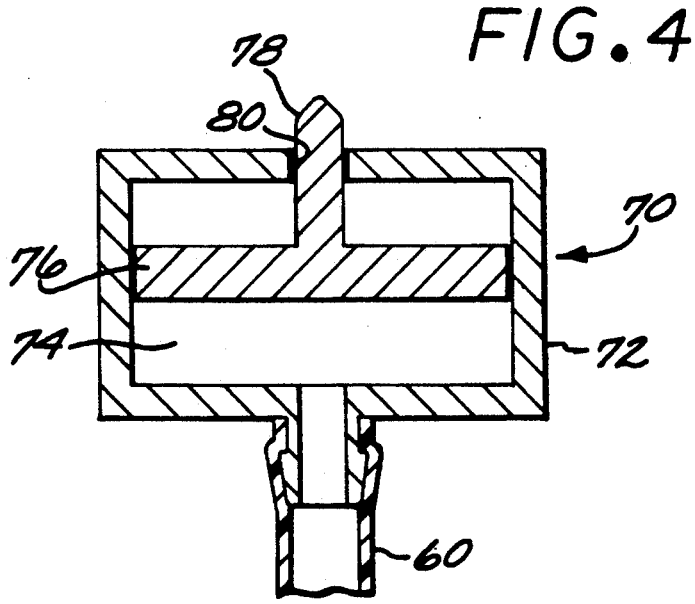
FIG. 4 is a side sectional view of another embodiment of the pressure chamber.

FIG. 4 illustrates another embodiment of tactile stimulator 70. The tactile stimulator 70 includes a body 72 with a pressure chamber 74. A piston 76 slides within the body 72. A probe 78 is affixed to the external surface of the piston 76 and extends through an opening 80 in the wall of the body 72. The probe 78 controllably extends from the body 72 of the pressure chamber 74 to mechanically contact the skin of the finger 42. The pneumatic pressure conduit 60 communicates between the interior of the pressure chamber 74 and the pressurization unit 62.

Figure 5:
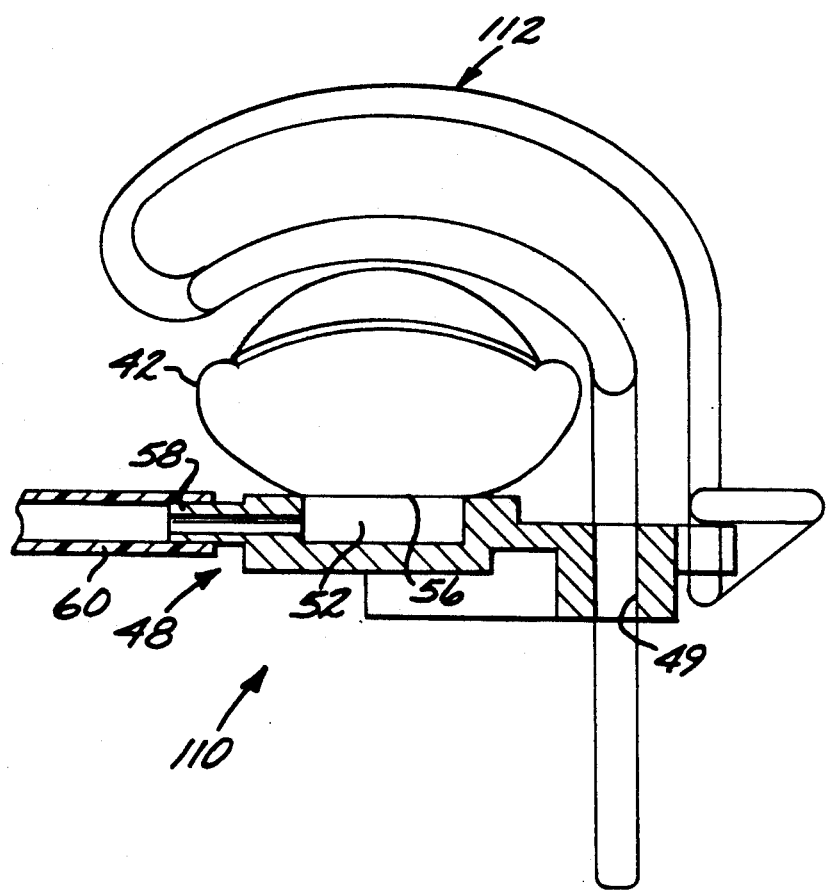
FIG. 5 is an end sectional view of another embodiment of the tactile stimulator.

FIG. 5 illustrates another embodiment of a tactile stimulator 110. Elements similar to those of the tactile stimulator 40 are similarly indicated. Instead of using the structure 44, 45, 46 to hold the body 48 in place, the tactile stimulator 110 uses a molded plastic beam 112. One end of the beam 112 is fixed to the body 48, and the other slides through the body 48 with a slip joint 49 like that described previously. The beam 112 is curved to define a space into which the finger 42 is inserted prior to the application of pressure. The application of pressure to the body 48 produces a tactile stimulation in the same manner as discussed in relation to the tactile stimulator 40.

Figure 6:
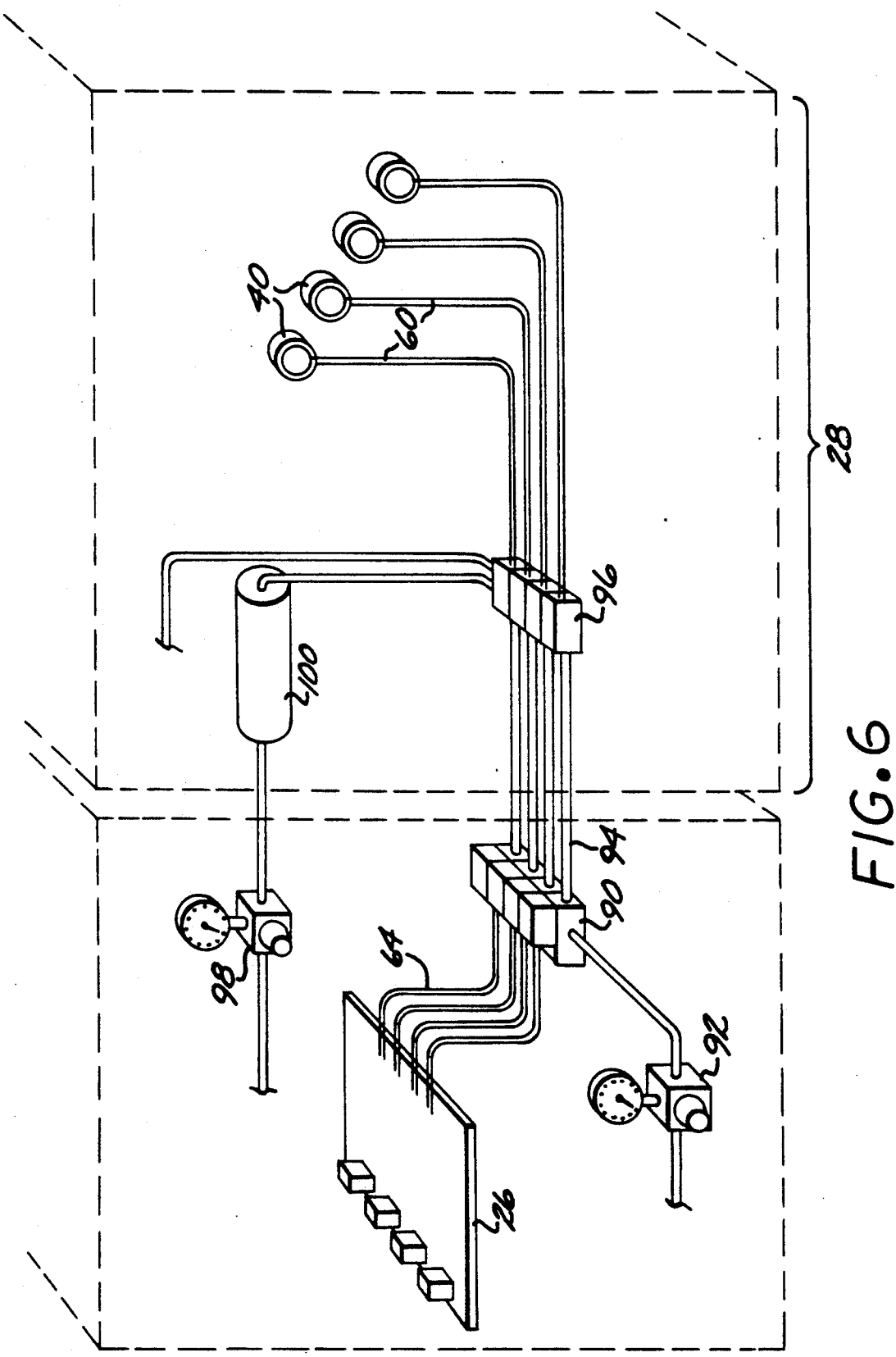
FIG. 6 is a schematic diagram of the preferred pneumatic system for the tactile stimulator.

FIG. 6 illustrates the pressurization unit 62 in greater detail. Since in many instances a plurality of tactile stimulators (e.g., one placed on each of several fingers) are used, FIG. 6 illustrates the arrangement used to activate four tactile stimulators 40. An electrically controlled pressure valve 90 receives command signals 64 from the computer 26. Such controllable valves 90 are available commercially, and a preferred valve 90 is a MAC 12 volt stacking valve Model Number 35A-5AAC-DOBA-1BA. This remotely controlled valve 90 has an input pressure supplied by a conventional manually controlled pressure regulator 92, which in turn is supplied from a source (not shown) such as a pressure tank. The available maximum output pressure on an output line 94 of the valve 90 depends upon the setting of the regulator 92.

The output line 94 extends through the wall of the shielded enclosure 28, where present, and may in fact serve as the conduit 60. However, if the distance from the pressurization unit 62 to the tactile stimulator 40 is large, an intermediate pressurization scheme may be used, as shown in FIG. 6. In this approach, the output line 94 provides a command signal to a pressure-controlled pressure valve 96. Such pressure-controlled valves 96 are available commercially, and a preferred valve 96 is a Clippard Model 2010. This valve is magnetically and electrically quiet, producing no fields or signals that can be detected directly by the measurement sensors 20 or 34. An input pressure to the valve 96 is provided from a manual pressure regulator 98, placed outside the enclosure 28 so as to be easily accessible, which in turn is supplied from a pressurized source (not shown). The duration of the pressure pulse applied to the stimulator 40 is controlled by the trigger duration from the computer 26 as the command signal 64. The pressure regulators 92 and 98 are available commercially, and a preferred regulator is the Master Pneumatics model R56-2LM-29. Optionally, the output pressure of the regulator 98 can be controlled by the computer 26, and a suitable commercially available computer-controlled regulator is the Robitech Model 890-1121. An accumulator 100 such as a Clippard accumulator model ATV-32-16 may be placed in the line between the regulator 98 and the valve 96, to reduce pressure fluctuations that might otherwise occur. The output of the pressure-controlled valve 96 is provided to the conduit 60, and in turn is supplied to the tactile stimulator 40.

The tactile stimulator 40 may be operated with any type of fluid medium, either a gas or liquid. For convenience and safety, pressurized air or pressurized nitrogen is preferred. In a preferred embodiment, the regulators 92 and 98 are supplied with air at 120 psi, and adjusted to output pressures of 0–5 psi (pounds per square inch) for the regulator 92, and 0–20 psi for the regulator 98. The pressure supplied to the tactile stimulator 40 or 70 ranges from 0 to a maximum of about 20 psi, although this range can be varied by resetting the pressure of the regulator 98.

The present approach provides a controllable mechanical force stimulation to the body in a manner that no magnetic or electrical fields are produced that may be detected directly by the measurement means. The apparatus is readily constructed in various forms as needed. Although a particular embodiment of the invention has been described in detail for purposes of illustration, various modifications may be made without departing from the spirit and scope of the invention. Accordingly, the invention is not to be limited except as by the appended claims.

What is claimed is:

1. Apparatus for measuring reactions of a living body of a subject, comprising:

means for measuring the bioelectromagnetic reaction of the living body of the subject to a tactile stimulation; and means for controllably stimulating the tactile stimulation on a surface of the living body without itself emitting magnetic or electric fields.

2. The apparatus of claim 1, wherein the means for measuring comprises biomagnetometer means including a magnetic field sensing coil for measuring magnetic fields arising from the living body of the subject.

3. The apparatus of claim 1, wherein the means for measuring comprises a detector of electrical signals.

4. The apparatus of claim 1, wherein the means for controllably stimulating includes a movable body, a fluid on one side of the movable body, means for delivering fluid pressure through the fluid to one side of the movable body; and means for generating the fluid pressure.

5. The apparatus of claim 4, wherein the means for delivering fluid pressure includes a fluid pressure chamber closed on one side by the movable body; and a conduit that transmits the fluid pressure to the pressure chamber.

6. The apparatus of claim 4, wherein the movable body is a piston.

7. The apparatus of claim 4, wherein the movable body is a flexible membrane.

8. The apparatus of claim 4, wherein the fluid is a gas.

9. The apparatus of claim 4, wherein the fluid is a liquid.

10. The apparatus of claim 1, further including means adapted for releasably attaching the means for controllably stimulating to the living body of the subject.

11. Apparatus for making measurements of the reaction of a living body of a subject to a tactile stimulation, comprising:

means for measuring a biomagnetic reaction of the living body to the tactile stimulation; and a tactile stimulator adapted to be attached to the living body, the tactile stimulator controllably applying the tactile stimulation against the body without creating a field that can be measured directly by the means for measuring, wherein the tactile stimulation is a mechanical force.

12. The apparatus of claim 11, wherein the means for measuring comprises a magnetic field sensing coil for measuring magnetic fields arising from the living body of the subject.

13. The apparatus of claim 11, wherein the tactile stimulator includes a pressure chamber closed on one side by a movable body, a conduit that transmits pressure to the pressure chamber, and means for applying a pressure to the conduit.

14. The apparatus of claim 13, further including a shielded room in which the living body of the subject is located.

15. The apparatus of claim 14, wherein the pressure chamber is located within the shielded room, the means for applying a pressure is located outside the shielded room, and the conduit passes from the exterior to the interior of the shielded room.

16. Apparatus for making biomagnetic measurements of a living body, comprising:

biomagnetometer means including a magnetic field sensing coil for measuring magnetic fields arising from the living body; and a tactile stimulator, including a pressure chamber, a movable body that closes one side of the pressure chamber, a conduit that transmits pneumatic pressure to the pressure chamber, and means for generating the pneumatic pressure in the conduit.

17. The apparatus of claim 16, further including a magnetically shielded room in which the living body is located, wherein the pressure chamber is located within the magnetically shielded room, and the conduit passes from the exterior to the interior of the magnetically shielded room.

18. The apparatus of claim 17, further including means located external to the magnetically shielded room for applying a controllable pneumatic pressure to the conduit.

19. The apparatus of claim 16, wherein the tactile stimulator further includes a probe attached to an exterior surface of the movable body.

* * * * *